United States Patent [19]

Jakosky, Jr. et al.

[11] 4,259,577
[45] Mar. 31, 1980

[54] METHOD AND MEANS FOR PREDICTING CONTENTS OF CONTAINERS

[75] Inventors: John J. Jakosky, Jr.; John J. Jakosky, both of Newport Beach, Calif.

[73] Assignee: The United States of America as represented by the Secretary of the Navy, Washington, D.C.

[21] Appl. No.: 26,918

[22] Filed: May 4, 1960

[51] Int. Cl.³ ................... G01N 23/00; G01N 23/20
[52] U.S. Cl. ................................ 250/358 R; 250/273
[58] Field of Search ...................... 250/50, 51, 52, 42, 250/61, 83.4, 83.6, 43.5, 358 R, 273

[56] References Cited

U.S. PATENT DOCUMENTS

| | | | |
|---|---|---|---|
| 2,315,819 | 4/1943 | Schlesman | 250/303 |
| 2,323,484 | 7/1943 | Neufeld | 250/269 |
| 2,370,163 | 2/1945 | Hare | 250/327.1 |
| 2,501,174 | 3/1950 | Herzog | 250/360 |
| 2,722,609 | 11/1955 | Morgan et al. | 250/252 |
| 2,769,097 | 10/1956 | Lord | 250/272 |
| 2,885,557 | 5/1959 | Kizaur | 250/360 |
| 2,997,586 | 8/1961 | Scherbatskay | 250/358 R |

*Primary Examiner*—Stephen C. Buczinski
*Attorney, Agent, or Firm*—Richard S. Sciascia; Joseph M. St. Amand; George J. Rubens

EXEMPLARY CLAIM

1. A method for detecting and differentiating between containers of submerged junk and explosive-filled mines in demolition operations, comprising the steps of subjecting an unknown submerged container under surveillance to a gamma radiation source, traversing said submerged container with said source along a standard diagnostic path, detecting the changes in intensity of the radiation penetrating the submerged container, and recording the variations of intensity of said radiation penetrating the submerged container along said path to obtain a density signature of said submerged container.

1 Claim, 11 Drawing Figures

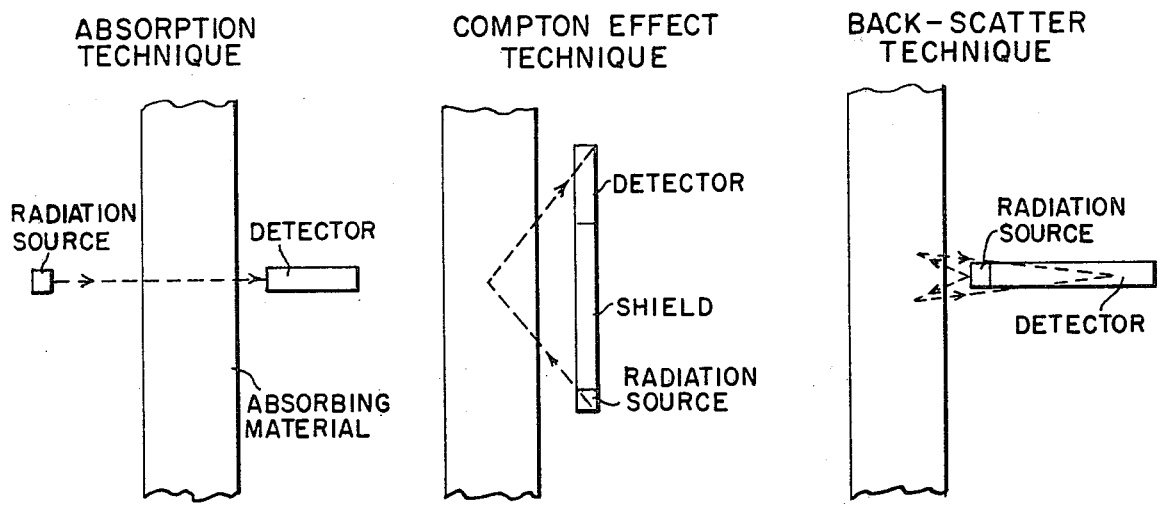
Fig. 1 ABSORPTION TECHNIQUE
Fig. 2 COMPTON EFFECT TECHNIQUE
Fig. 3 BACK-SCATTER TECHNIQUE
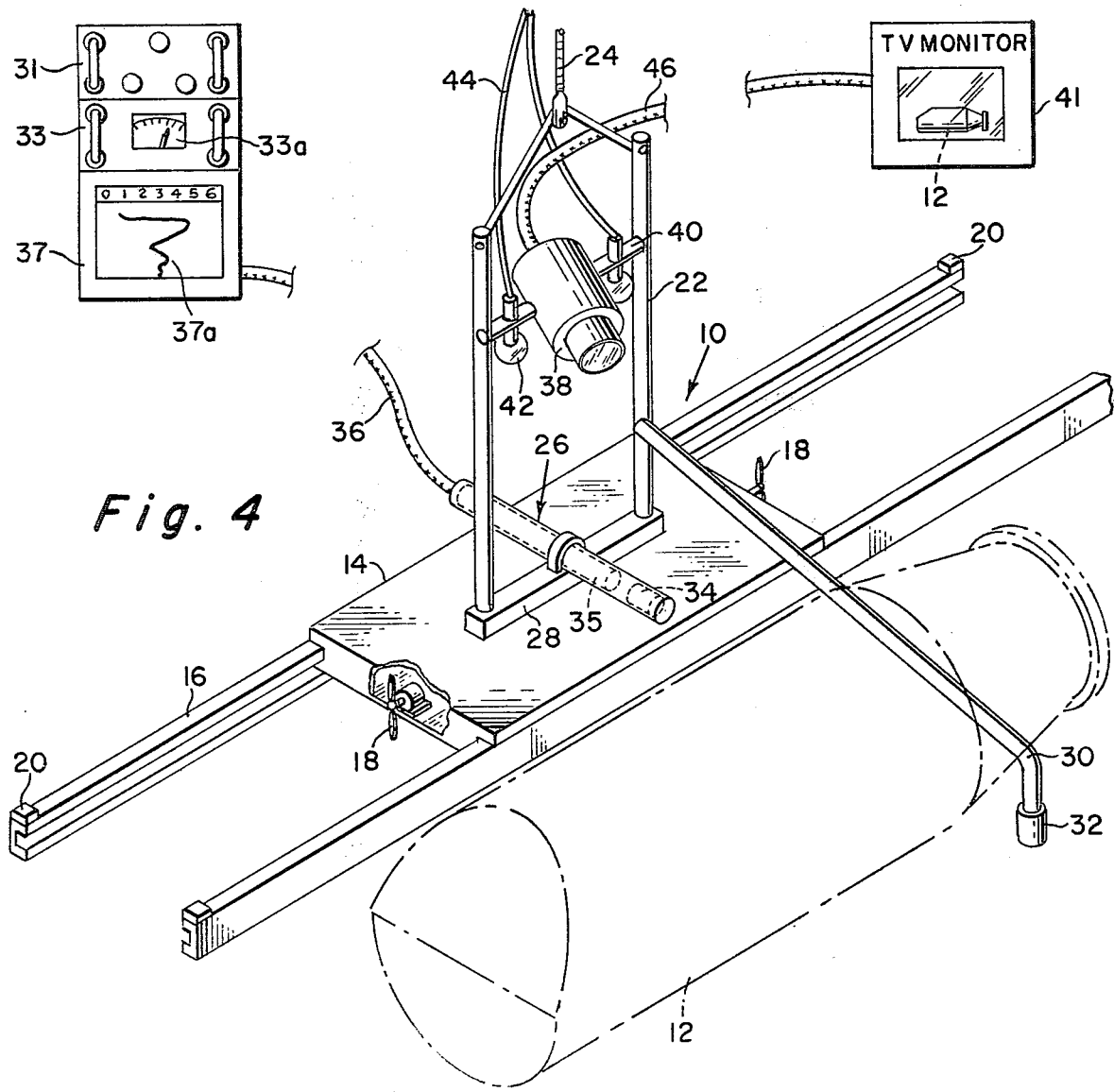
Fig. 4

MINE CASE IN AIR
FILLED WITH AIR
FIRING MECHANISM
REMOVED

MINE CASE IN AIR
FILLED WITH WATER
FIRING MECHANISM
INSTALLED

MINE CASE IN AIR
FILLED WITH EXPLOSIVES
FIRING MECHANISM
REMOVED

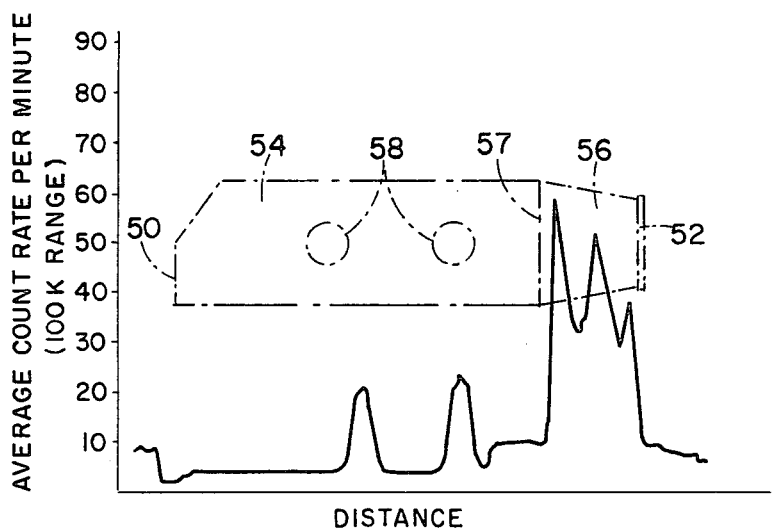
MINE CASE IN SEA WATER FILLED WITH EXPLOSIVES FIRING MECHANISM REMOVED.
Fig. 8
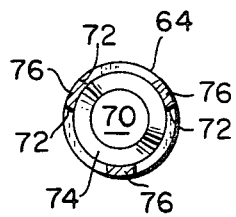
Fig. 10
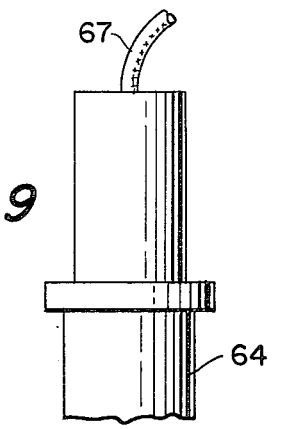
Fig. 9
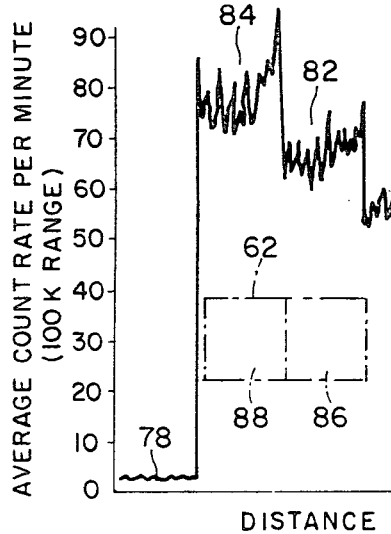
Fig. 11
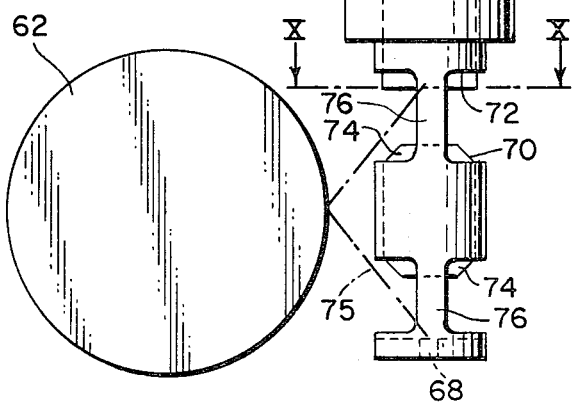

METHOD AND MEANS FOR PREDICTING CONTENTS OF CONTAINERS

This invention relates to exploration methods utilizing a radioactive substance, and more particularly to a method and means for detecting and differentiating the contents of unknown containers through the use of a radioactive source, for example, to determine whether the container is submerged junk containing sea water or a loaded mine case containing explosive material.

In underwater demolition work and in the removal of underwater obstacles from harbors, etc., it is imperative to obtain a positive and quick identification of the contents of the obstacle or container instead of relying on the technique of visual evaluations now employed. Visual means at most may identify the outer configuration of a known container, but such method is of no assistance in identifying the contents of known or unknown containers. The material contents of a container, i.e., explosives vs water will dictate entirely different procedures for disposal, affecting the expenditure of money and time. Furthermore, if the container contents is an explosive, visual inspection may present a dangerous environment to the diver.

Another critical situation wherein identification of the contents of a known container is of prime importance is in rescue operation involving a submerged vessel, such as a submarine, where it is necessary to determine whether a specific compartment is flooded and the extent of the flooding.

Although means employing radioactive rays have been used for underground oil exploration purposes, no prior art method or means for detecting and differentiating the contents of containers such as explosive material and sea water, by employing a radioactive source, has been suggested or devised.

For example, a so-called "neutron" method has been employed for stratagraphic logging of drill and bore holes of oil wells. A logging of the degree of absorption of the neutron travel into the adjacent earth strata as the instrument travels through the bore is a measure of the amount of hydrogen in the adjacent formation. A higher hydrogen content is indicated by a higher absorption. However, this technique is not suitable to solve the instant problem because of the vast numbers of hydrogen atoms in both sea water and explosives, and the difficulty to distinguish any differential in counts of these two materials in the presence of each other as would occur in practice.

Other similar techniques are used to determine the moisture content in the lumber industry, and for other uses in food processing and general chemistry but none will solve the problem at hand.

It has been discovered that a technique utilizing a radioactive source, particularly gamma radiations, will provide a suitable means for differentiating between submerged junk that may be filled with water, and explosive-loaded mine cases. This technique resides in measuring the change in intensity of a beam of gamma radiation penetrating an object or material under investigation. One method under this technique is to measure the amount of absorption of the gamma rays as they pass directly through the object. Another method is to measure the scattering of the gamma rays, the so-called Compton effect, by the material adjacent to the source of gamma rays and a detector. Still another method is to measure the amount of back-scatter caused by the various objects or materials.

Since the various known explosive mines have different internal structural arrangements, i.e., air gaps, partition walls, explosive portions, triggering devices, etc., which occupy part of the mine case, it is possible because of differences in density of the material of these portions to obtain a radiographic film showing these structures. Each type of mine will have its own peculiar signature thus providing a positive identication.

One type of predictor for carrying out the absorption method under this technique comprises a fixed source of gamma rays and a detector spaced apart so that the container under examination can be positioned directly therebetween. The amount of absorption of the gamma rays passing through the container would indicate the type of material contained therein, as the degree of absorption is a function of the density of the material. A high count rate indicates low density materials, and a low count rate indicates high density materials.

This inverse relationship between count rate and density in the absorption technique should be distinguished from the Compton scattering technique wherein the count rate increases as the density of the material increases.

The predictor may be a hand guided unit carried by a diver, or a remotely controlled probe suspended by a cable from a ship and guided by means of a closed underwater television system. The remotely guided predictor assembly can be mounted on tracks or the like to enable the container to be transversed end-to-end with the radiation source to obtain a signature or radiation absorption profile of the container.

A predictor based on the Compton scattering technique can be simple compared to aforedescribed predictor used in the straight absorption technique in that in the former predictor the gamma radiation source and the detector can be positioned on the same side of the container rather than on opposite sides of the container as in the latter predictor.

A principal object of this invention is to provide a method and device for predicting the contents of containers.

Another object is to provide such means whereby a submerged container filled with explosives, i.e., a mine, can be distinguished from a container which may be debris containing water, sand etc.

A further object is to provide a method and device whereby a radiation absorption profile can be obtained of such a container to enable positive identification with a known container.

Still another object is to devise a device for predicting the contents of submerged containers which can be hand-supported and controlled, or remotely supported and controlled.

Other objects and many of the attendant advantages of this invention will be readily appreciated as the same become better understood by reference to the following detailed description when considered in connection with the accompanying drawings wherein:

FIG. 1 is a diagrammatic illustration of an absorption method of measuring the amount of radiation absorbed by material positioned between a gamma ray source and a detector;

FIG. 2 is a diagrammatic illustration of a scattering method of measuring the amount of radiation by the Compton scattering effect, the gamma ray source and the detector being positioned on the same side of the material;

FIG. 3 is a diagrammatic illustration of a back-scatter method;

FIG. 4 is a perspective view of a remotely controlled predictor device utilizing the direct absorption method on a submerged mine case being investigated;

FIGS. 5, 6, 7 and 8 show gamma radiation absorption profiles of a MK 25-MOD 2 mine case filled with representative materials using the predictor illustrated in FIG. 4.

FIGS. 9 and 10 are elevation and cross-sectional views, respectively, of a predictor utilizing the Compton scattering effect method; and FIG. 11 shows gamma radiation scattering curves of various sections of a container taken under water with the predictor of FIG. 9.

Figure 5:
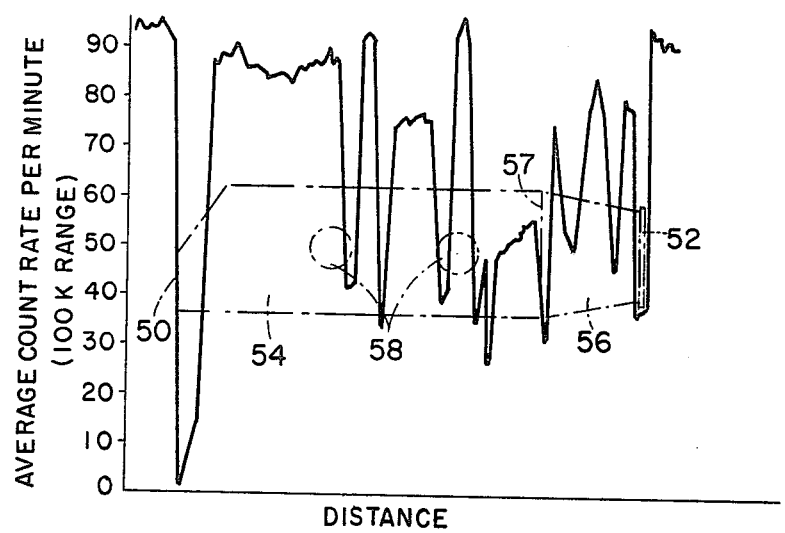

Gamma radiations provide a unique and versatile technique for predicting the contents of unknown containers, and particularly distinguishing between submerged junk and explosive-loaded mine cases. FIGS. 1 to 3 diagrammatically disclose different absorption techniques for accomplishing these results. It was found that a detectable difference in absorption, using the technique of FIG. 1, was obtained when gamma rays were passed through various materials, i.e., salt water, explosives, sand, aluminum, steel, etc., which materials are those associated with and/or used in the construction of mines. In other words, the amount of gamma ray absorption primarily is a function of the density of the material. A high count rate indicates low density materials and a low count rate indicates high density materials.

The amount of absorption will follow the well known absorption law, $I = I_o e^{-ux}$, provided the measurement does not include scattered radiation which would tend to decrease the apparent absorption coefficient. However, errors due to scattered radiation can be reduced by collimation.

Measurements were made on the various aforementioned materials using as the sources of gamma-ray energy, radioactive cobalt 60 with a half-life of 5.3 years; and cesium 137 having a half-life of 33 years. Both of these radioactive isotopes are readily available. The test procedure comprised measurement of the amount of radiation reaching the detector without any absorbing material, followed by radiation measurements through increasing thicknesses of the absorbing material under test. Because of the random disintegration of radioactive substances, the Binary scaler was allowed to operate until approximately 30,000 counts had been recorded, thus reducing the statistical error in measurements. Ten measurements were made in each sample size. An average of the ten determinations provided an average number of counts per minute which then could be plotted against the sample thickness.

Because the absorption law follows an exponential decay the data was plotted on two-cycle semi-log graph paper, producing a straight line. From these curves, the thickness of absorbing material required to decrease the number of photons reaching the detector by one-half could be read directly from the graph (not shown). Using these values the linear absorption coefficients for each of the test materials were computed as appears in the following table No. 1:

| MATERIAL | RADIO-ACTIVE SOURCE | HALF-THICKNESS INCHES | HALF-THICKNESS CM | LINEAR ABSORPTION COEFFICIENT |
| --- | --- | --- | --- | --- |
| Aluminum | Cobalt 60 | 1.68 | 4.26 | .1629 cm$^{-1}$ |
| Brass | Cobalt 60 | .55 | 1.39 | .496 |
| Carbon Tetrachloride | Cobalt 60 | 2.88 | 7.31 | .0934 |
| Douglas Fir | Cobalt 60 | 6.0 | 15.23 | .0454 |
| 40% Gelatin Extra | Cobalt 60 | 2.4 | 6.1 | .1135 |
| SAE 30 Oil* | Cobalt 60 | 4.4 | 11.18 | .062 |
| Dry Sand | Cobalt 60 | 2.75 | 6.98 | .0992 |
| Moist Sand | Cobalt 60 | 2.14 | 5.43 | .1277 |
| Mild Steel | Cobalt 60 | .60 | 1.52 | .454 |
| Salt Water | Cobalt 60 | 3.75 | 9.52 | .0727 |
| Tap Water | Cobalt 60 | 3.80 | 9.65 | .0718 |
| Aluminum | Cesium 137 | 1.3 | 3.3 | .210 |
| Brass | Cesium 137 | .40 | 1.01 | .682 |
| Carbon Tetrachloride | Cesium 137 | 2.07 | 5.26 | .1318 |
| Douglas Fir | Cesium 137 | 4.70 | 11.92 | .0581 |
| 40% Gelatin Extra | Cesium 137 | 1.68 | 4.26 | .1625 |
| SAE 30 Oil | Cesium 137 | 3.24 | 8.23 | .0842 |
| Dry Sand | Cesium 137 | 2.03 | 5.16 | .134 |
| Moist Sand | Cesium 137 | 1.57 | 3.98 | .174 |
| Mild Steel | Cesium 137 | .42 | 1.068 | .650 |
| Salt Water | Cesium 137 | 2.83 | 7.18 | .096 |
| Tap Water | Cesium 137 | 2.97 | 7.55 | .091 |

*Refined 100% Pure Paraffin Base Oil

The remotely controlled predictor 10 shown in FIG. 4 incorporates the absorption technique of FIG. 1, and is particularly suited for obtaining surface measurements of submerged containers such as a mine case 12. The predictor comprises an assembly of a carriage 14 movable back-and-forth on a pair of spaced parallel tracks 16 by a pair of oppositely disposed motor-driven propellers 18 mounted on the carriage. Obviously other means for driving the carriage can be employed. Movement of the carriage on the rails is limited between stops 20. It is believed that a carriage movement of approximately one inch per minute would be a suitable speed for scanning purposes in most instances, which speed may be made variable. A tubular frame 22 bolted to the carriage enables the entire assembly to be suspended and positioned adjacent mine case 12, or any other container to be investigated, by a hoisting cable system 24 controlled from a surface vessel or other remote station (not shown).

A scintillation detector unit 26 is clamped on a base 28 of the frame transversely the carriage and disposed diametrically on one side of mine case 12. On the opposite side of the mine case and supported on the end of an arm 30 mounted on the frame is a suitable gamma-ray radiation source 32. Detector unit 26 comprises a Sodium-Iodide, Thallium activated crystal 34 located in a front end of an underwater housing and optically coupled to an adjacent photomultiplier tube 35 electrically connected by conductors 36 to conventional recording apparatus carried on the surface craft. Such apparatus may consist of a radiation analyzer 31, a count rate meter 33, and a chart recorder 37.

In the event the predictor is not controlled by a diver, as would be the case in the apparatus of FIG. 4, a closed-circuit television system connected between the surface station and predictor 10 may be employed to facilitate the positioning by the operator of the carriage and track assembly adjacent a submerged container to be scanned. In FIG. 4, an underwater camera 38 of the television system is gimbalmounted by cross tube 40 of the frame, and is oriented to give a viewing coverage at T-V monitor 41 on the vessel of both detector unit 26 and the container under study. An underwater light 42 (i.e. 1,000 watt) is also mounted on each cross tube 40, one on each side of the camera, to illuminate the area to be viewed. The underwater lights 42 are electrically connected by cable 44 to a source of power on the vessel, and T-V camera is connected to its T-V monitor by coaxial cable 46. The camera housing may be magnetically shielded in a conventional manner to minimize any magnetic effect the camera may have on mines using magnetic-type firing mechanisms.

The invention methods illustrated in FIGS. 1–3 may be carried out manually by a diver or remotely by apparatus such as is disclosed in FIG. 4.

For investigating a submerged mine 12, predictor 10 is lowered from a vessel by hoisting cable 24 and through the aid of the closed-circuit television system, the scanning rails are positioned parallel to the longitudinal axis of the mine case with the mine located intermediate the ends of the rails. In this position the mine is straddled between gamma radiation source 32 and detector 26 so that the rays from the former can travel diametrically through the mine and be picked up by the detector. When the predictor is appropriately positioned around mine case 12, the carriage is moved to a starting point beyond one end of the mine case and the carriage continuous drive mechanism is set in operation so that the source-detector assembly on the carriage slowly and uniformly traverses the entire length of the mine.

Although intermittent reading can be obtained at selected intervals along the mine case, it has been found preferrably to use a continuous scanning movement to provide sufficient details of the various internal structural aspects of containers, especially mine cases.

The disintegration rate of the radioactive material from gamma ray source is a random phenomenon, and the rate meter circuits provide a means of converting these random pulses into an average number of counts per minute for presentation on the panel meter 33a. Simultaneously, the average count rate is recorded on chart 37a of recorder 37.

Figure 6:
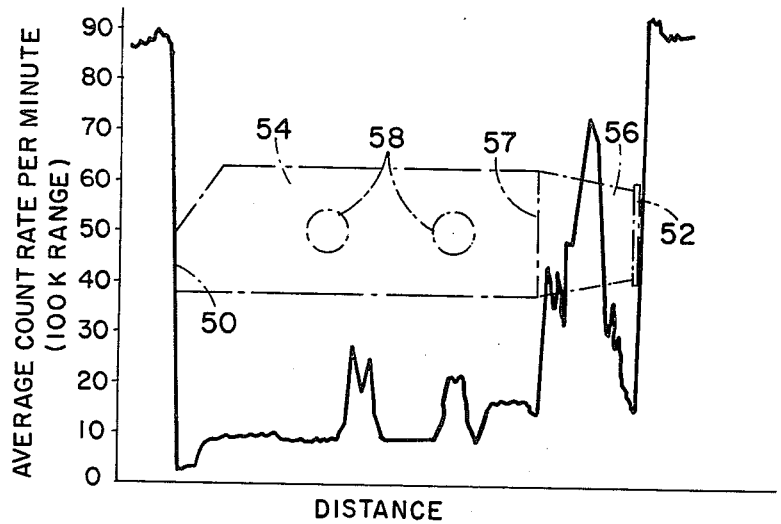
Figure 7:
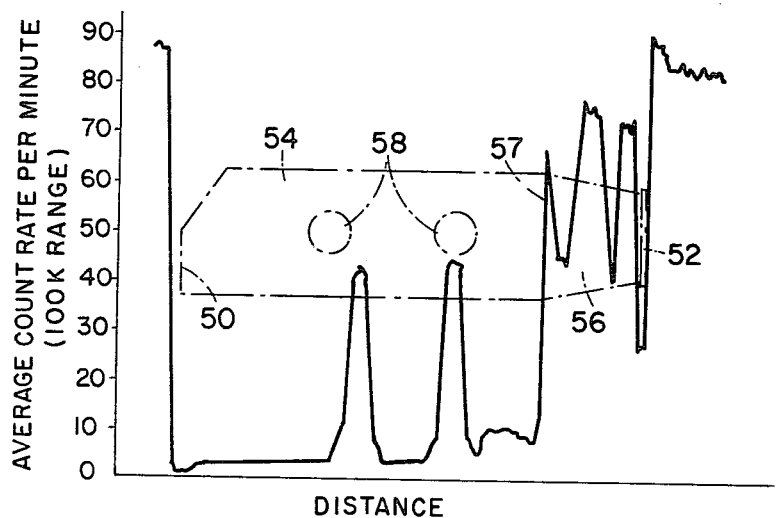

As the predictor scans the entire length of the submerged mine case 12 and slightly beyond, a synchronous profile is obtained which shows the variations in gamma ray absorption. Such absorption profiles are shown in FIGS. 5–8 wherein an outline drawing of mine case 12 is shown in phantom lines in order that correlation between count rate and longitudinal mine construction, abscissa and ordinate, respectively, may be observed. In FIGS. 5–7, mine case 12 was in an atmospheric environment being positioned on the ground, whereas in FIG. 8 the mine case was submerged 25 feet in sea water.

In each of the profiles illustrated in FIGS. 5–8, the gamma radioactive source employed was cobalt 60 which source was spaced 24 inches from the detector. Mine case 12 is a typical representative Navy mine; i.e. MK 25-MOD 2 and was used in the profiles of FIGS. 5–8. Mine case 12 is made of brass and contains two end bells 50 and 52, with intermediate explosive compartment 54 and an instrument compartment 56 separated by bulkhead 57 (FIG. 5). Recessed ports 58 in the case accomodate the firing mechanism (not shown).

In each profile of FIGS. 5, 6 and 7, the respective absorption curve shows a high count rate off the ends of mine case 12 due to absence of any other absorbing material, other than air, between the source and the detector. Variations in absorption along the mine case between the ends are characteristic of the particular mine case due to its individual or unique construction, and the invention thereby provides a diagnostic means for predicting the contents of the case.

For example in FIG. 5 mine case 12 was filled with air. As predictor 10 passed over the instrument end (from right to left in the drawing), the count rate dropped rapidly over bell end 52, because of the concentration of metal, and then rose through the empty instrument compartment 56. Because compartment 54 was empty, that is air filled, a high count rate was present in this area which normally contains explosive material; however, variations in this section are caused by the empty ports 58 which normally contain the firing mechanism and in the metal of bulkhead 57. When the predictor passed over case end 50 another low count rate was obtained as on end 52. The count rate rose rapidly as the predictor traveled in air only beyond the case.

In FIG. 6, compartment 54, normally filled with explosives, was filled with water and the firing mechanism was installed in ports 58. In comparison with the profile in FIG. 5, the profile of FIG. 6 clearly shows the effect of the presence of the water and the instruments by a lower count rate. Large fluctuations along the profile are present, however, due to void air spaces in the instrument end 56.

In FIG. 7, the firing mechanisms in ports 58 were removed and the compartment 54 filled with an equivalent explosive-like material instead of water as in FIG. 6. Because of the greater density of the explosive-like material, a still lower count rate was recorded except for the areas adjacent ports 58.

As previously mentioned, in FIGS. 5–7 the absorption profiles were obtained by testing the mine case in air. In FIG. 8, a profile was obtained with the mine case used in FIG. 7, however, submerged in 25 feet of sea water. As in the previous tests the profile was made by starting a short distance away from the case end 50, traversing the entire length and continuing a short distace beyond case end 52. The initial increased absorption on the FIG. 8 curve before end 52, as compared with the profiles in FIGS. 5–7, is due to the mass of salt water between the detector and the radiation source, the absorption rate decreasing as the detector passes over end 50. Although compartment 54 is filled with the explosive-like material, the absorption rate is slightly higher except for rapid increases at the areas adjacent empty instrument ports 58 (the high peaks represent decreased amount of absorption). As the predictor reaches instrument compartment 56, the amount of absorption rapidly decreases due to the decreased density of the air-filled compartment, with variations in absorption caused by the bulkheads in the case. The absorption gradually increases as the diameter of compartment 56 decreases until the predictor passed beyond case end 52 where the absorption of the salt water is the same value as the area off the other end of the case. Although the absorption profile was obtained in salt water at a depth of 25 feet, the same type of profile should be obtained at any depth of water since the density of sea water remains substantially constant with depth. The results shown in FIGS. 5–8 inclusive indicate that the same degree of detail in the absorption profiles may be obtained in the underwater detection (FIG. 8), as that obtained when the mine case is in air (FIGS. 5–7). These profiles reveal that changes in density of the contents within a container can be predicted by measuring the absorption of gamma rays passing directly through the container. A high count rate indicates low desity materials (a low amount of absorption), and a low count rate indicates high density materials (a high amount of absorption).

Expeditious and precise positioning of predictor 10 of FIG. 4 for underwater absorption profiles from a boat required may present some problems in situations where tide, wind and wave may adversely affect the motion of the boat. In such instances a predictor 60 of FIG. 9 may be employed which utilizes the Compton scattering technique diagrammatically illustrated in FIG. 2. The advantages of this technique is that measurements need only be made from one side of the container, and, therefore, the source-detector probe does not have to straddle the mine or container 62, as in the straight absorption technique in FIG. 1. In addition, predictor 60, being more compact, can easily be carried by a diver if direct, rather than a remote, approach is preferred. The measurement of density by this method is based on the interaction of gamma rays and the orbital electrons of atoms. A material placed near a source of gamma rays, causes scattering due to its presence and by placing a gamma ray detector at a fixed distance from the source, it is possible to observe the number of gamma rays being scattered toward and reaching the detector per unit of time.

As the number of electrons per unit of volume of scattering medium is increased, the scattering power of the medium increases in proportion. With each scattering process the gamma ray loses some of its energy. With an increase in electron density the probability of multiple scattering of the gamma ray increases, and also the probability that the gamma ray will be absorbed is increased.

The combined effect of these probabilities is that for a scattering medium of either zero or infinite density no gamma rays will reach the detector, and that a maximum number of rays will reach the detector at some intermediate density. The density at which this maximum count rate will appear depends on the longitudinal distance between the radiation source and the detector. The distance between the source and the detector is a function of the angle of penetration, the depth of penetration, and the lateral distance the predictor is positioned from the container.

Predictor 60 comprises an underwater tubular housing 64, one end which houses a detector 66 provided with conductor 67 to the suitable recording apparatus as in FIG. 4. The other end of housing 64 supports a gamma-ray source 68, such as cesium 137. Spaced between detector 66 and gamma-ray source 68 is a lead plug 70 secured in the housing, the plug functioning to mask off direct radiation therebetween and, thereby avoid high background count.

Housing 64 has cut-out portions 72 adjacent both ends of plug 70 to permit unrestricted passage of the gamma rays, diagrammatically illustrated at 75, the edges of plug 70 being beveled at 74 also to avoid interference with the rays. The remaining portions of the housing form spaced arms 76.

Predictor 60 is employed to obtain similar results as predictor 10, namely, to obtain density signatures similar in effect to the curves of FIGS. 5–7. The scattering curve in FIG. 11 was obtained by positioning predictor 60 adjacent various portions of the container 62 as in FIG. 9, container 62 being shown in FIG. 11 by phantom lines. In the curve of FIG. 11, container 62 was located in 25 feet of sea water. The end portions 78 of the scattering curve in FIG. 11 show a small count rate when predictor was suspended in free air. Portion 80 of the curve indicates a higher count rate when the predictor was suspended in the sea water, while portions 82 and 84 show the count rate when the predictor was positioned adjacent the instrument end 86 and the filled explosive end 88 of the submerged container 62. These curves show an increase in the amount of radiation reaching the detector expressed in count rate with a increase in density of the material adjacent to the detector.

Predictor 60 used to obtain the scattering curve of FIG. 11 was constructed with a spacing between detector and radiation source of approximately 10 inches, and the predictor was maintained about 3 inches from the container. Measurements should be made, as before, in a systematic manner along a diagnostic path, and preferrably in a transverse direction along a longitudinal axis of the container.

An instrument capable of indicating whether a container or compartment filled with air or water may have good use in submarine rescue operations. By positioning the source-detector unit at various points along the submarine hull it will be possible to obtain a direct and immediate indication as to whether a particular compartment is flooded or not, and the extent of the flooding.

The present invention provides a safe and reliable method for exploring and predicting contents of unknown containers, such as distinguishing between submerged junk and loaded mine containers. This method provides a direct control technique in which the probe can be hand carried by a diver, or a remote control wherein the source-detector probe can be positioned from a boat and observed through a closed-circuit television camera. By scanning the entire length of the container with the source-detector probe along a diagnostic path and recording the absorption profile, a density signature can be obtained which will positively identify known container and contents and thus enable safe prediction.

Obviously many modifications and variations of the present invention are possible in the light of the above teachings. It is therefore to be understood that within the scope of the appended claims the invention may be practiced otherwise than as specifically described.

We claim:

1. A method for detecting and differentiating between containers of submerged junk and explosive-filled mines in demolition operations, comprising the steps of subjecting an unknown submerged container under surveillance to a gamma radiation source, traversing said submerged container with said source along a standard diagnostic path, detecting the changes in intensity of the radiation penetrating the submerged container, and recording the variations of intensity of said radiation penetrating the submerged container along said path to obtain a density signature of said submerged container and contents enabling a positive identification of said unknown submerged container by comparison of its density signature with density signatures of known containers.

* * * * *